United States Patent [19]

Tsujimoto et al.

[11] Patent Number: 5,763,560
[45] Date of Patent: Jun. 9, 1998

[54] METHOD OF PRODUCING STYRENE DERIVATIVES

[75] Inventors: Kenzo Tsujimoto; Yoshiharu Ayabe; Fujihisa Matsunaga, all of Wakayama; Ikuzo Nishiguchi, Hirakata; Yoshio Ishino, Kyoto, all of Japan

[73] Assignees: Honshu Chemical Industry Co., Ltd., Tokyo; Osaka Municipal Government, Osaka, both of Japan

[21] Appl. No.: 642,823

[22] Filed: May 3, 1996

[51] Int. Cl.$^6$ ............................................ C08G 4/00
[52] U.S. Cl. ........................ 528/234; 528/230; 528/247
[58] Field of Search ............................ 528/230, 234, 528/247

[56] References Cited

U.S. PATENT DOCUMENTS

| | | | |
|---|---|---|---|
| 3,865,848 | 2/1975 | Nystad | 260/346.1 M |
| 4,013,643 | 3/1977 | Nystad | 260/240 K |
| 4,585,898 | 4/1986 | Lau et al. | 568/433 |
| 4,603,101 | 7/1986 | Crivello | 430/270 |
| 5,082,966 | 1/1992 | Moffat | 560/11 |

FOREIGN PATENT DOCUMENTS

| | | | |
|---|---|---|---|
| 0102450 | 3/1984 | European Pat. Off. | C07C 7/08 |
| 0486267 | 11/1991 | European Pat. Off. | C07C 69/96 |
| 1106834 | 4/1989 | Japan | C07C 43/188 |
| 1106835 | 4/1989 | Japan | C07C 43/188 |
| 4253939 | 9/1992 | Japan | C07C 69/96 |
| 5201912 | 8/1993 | Japan | C07C 43/215 |
| 8303698 | 4/1983 | WIPO | C09G 3/28 |

OTHER PUBLICATIONS

K. Takai et al. "Effective methods of carbonyl methylenation using CH2I2-Zn-Me3A1 and CH2Br2-Zn-TiCl4 system," Tetrahedron Letters, No. 27, 1978 pp. 2417-2420.

Various, "Kureze Originalmitteilungen," Zeitschrift fur Chemie, 1/64, pp. 27-37.

Frechet, Eichler, Ito and Wilson, "Poly(p-tert-butoxycarbonyloxystyren): a convenient precursor to p-hydroxystyrene resins", Polymers, Aug. 1983, pp. 995-1000.

B.B. Carson et al., "Preparation of Vinylphenols and Isopropenylphenols," Journal of Organic Chemistry, vol. 23 1958, pp. 544-549.

W.J. Dale and H.E. Hennis, "Substituted Styrenes. III. The Syntheses and Some Chemical Properties of the Vinylhenols", Journal of American Chemistry Society, Jul. 20, 1958, pp. 3645-3649.

*Primary Examiner*—Duc Truong
*Attorney, Agent, or Firm*—Fulbright & Jaworski L.L.P.

[57] ABSTRACT

A method of producing styrene derivatives expressed the general formula (2) by reacting a benzaldehyde derivative expressed by the general formula (1) with dibromomethane under the existence of zinc metal as well as an active chloride for producing various types of oxystyrene which are polymerized monomers as a photoresist material used in a high density integrated circuit process from easily available materials which also can easily be handled:

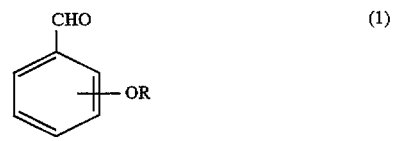

(1)

(wherein R indicates a an alkyl group, alkoxyalkyl group, an alkylcarbonyl group, an alkoxycarbonyl group, a 5 or 6-atom heterocylclic groups, or an alkylsilyl group);

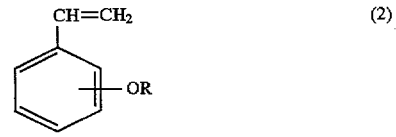

(2)

(wherein R indicates any of the same substituents as those described above.)

14 Claims, No Drawings

METHOD OF PRODUCING STYRENE DERIVATIVES

BACKGROUND OF THE INVENTION

1. Field of the Invention

The present invention relates to a method of efficiently producing substituted oxystyrene derivatives used as a monomer for polymerization for synthesizing poly (hydroxystyrene) which is a useful material as a photoresist material or as an electron beam resist material.

2. Prior Art

In recent years semiconductor devices have been becoming increasingly smaller with the integration degree getting higher and higher, and an increasingly higher resolution and high adaptability to development are required to resist materials for lithography. To satisfy this demands, as an alternative for the novolak resin, chemically amplifying type of resist materials for a short wavelength light such as those generated by KrF, or ArF eximer lasers. As the resist materials, those having a protection group which is easily acidolysised by an acid generated when exposed to light and also having different solubilities before and after acidolysis of the protection group are preferred. As the resist materials as described above, poly(hydroxystyrene) derivatives having high anti-plasma resistance have been known as preferable ones. And, as a monomer used to produce the poly (hydroxystyrene) derivatives, a substituted oxystyrene derivative in which a hydroxyl group in the hydroxystyrene is protected by a protection group which can easily be acidolysised by an acid.

At present various types of production method are known as a method of producing the substituted oxystyrene derivatives.

The production methods based on the conventional technology can largely be classified as follows.

1) A method in which a p-substituted oxystyrene is produced as a raw material for phenols a) J.Org.Chem.23,544 (1958) discloses a method in which phenol is reacted with acetic acid in the presence of trifluoroboron to produce p-hydroxyacetophenone, the p-hydroxyacetophenone is acetylated to p-acetoxyphenylmethylcarbinol, which is dehydrated in the presence of potassium hydrogen sulfate catalyst to obtain p-acetoxystyrene.

b) Japanese patent laid-open publication No. 201912/1993 discloses a method in which p-chlorophenol is reacted with sodium methylate for the hydroxyl group to be substituted with a sodium salt, the resultant product is reacted with chloromethyl ether to obtain p-methoxymethoxychlorobenzene, the p-methoxymethoxychlorobenzene is reacted with magnesium in a tetrahydrofuran solvent to obtain the Grignard reagent which is coupled with vinyl bromide to obtain p-methoxymethoxystylene.

2) Method of producing p-substituted oxystyrene from p-substituted styrene a) U.S. Pat. No. 5,082,966 discloses a method in which potassium hydroxide is reacted with p-acetoxystyrene, and the resultant compound is reacted in the presence of a phase transfer catalyst to di-tert-butyldicarbonate to obtain p-tert-butoxycarbonyl oxystyrene.

b) EU Patent No. 486,267 discloses a method in which potassium hydroxide is reacted in a ethyl acetate solvent with p-acetoxystyrene, and the resultant compound is reacted with di-tert-butyldicarbonate to obtain p-tert-butylcarbonyl oxystyrene.

c) Japanese Patent Laid-Open Publication No. 253939/1992 discloses a method in which potassium-tert-butoxide, and then the resultant composition is reacted with di-tert-butyldicarbonate to obtain p-tert-butoxycarbonyl oxystyrene.

d) U.S. Pat. No. 4,603,101 discloses a method in which p-chlorostyrene is converted to a Grignard reagent and then is reacted with tert-butylperbenzoate to obtain p-tert-butyloxystyrene.

3) Method of producing p-substituted oxystyrene from p-hydroxy benzaldehyde

EU Patent No. 102,450 discloses a method in which potassium tert-butoxide is reacted with p-hydroxybenzaldehyde, then the resultant compound is reacted to di-t-butyldicarbonate to obtain p-tert-butoxycarbonyloxy benzaldehyde, which is subjected to the Wittig reaction where the compound is reacted to methyl bromide triphenylphosphine to obtain p-tert-butoxycarbonyloxystyrene.

4) Method of producing p-substituted oxystyrene from p-substituted oxybebzaldehyde a) J. Am. Chem. Soc., 80,3645 (1985) discloses a method in which p-acetoxybenzaldehyde is methylenated using the Grignard reagent to obtain p-acetoxystyrene.

b) Z. Chem. 4, 30 (1964) discloses a method in which p-trimethylsilyl benzaldehyde is methylenated using the Grigrard reagent to obtain p-trimethylsilyl oxystyrene.

c) Polymer, 24, 995 (1983) discloses a method in which p-acetoxy benzaldehyde is subjected to the Wittig reaction where the compound is reacted to methyl bromide triphenylphosphine to obtain p-acetoxystyrene.

5) Method of producing p-tert-butoxystyrene from p-tert-butoxychlorobenzene

Japanese Patent Laid-Open Publication No. 106835/1989 discloses a method in which p-tert-butoxychlorobenzene is reacted to the Grignard reagent, and then the resultant compound is reacted with vinyl chloride in the presence of nickel phosphine complex to obtain p-tert-butoxystyrene.

SUMMARY OF THE INVENTION

In the conventional methods of producing substituted oxystyrene derivatives as described above, there are various disadvantages including use of expensive reagents such as the Grignard reagent and Wittig reagent and necessity of facilities and operations for specific reactions. Furthermore the yield is not so high.

It is an object of the present invention to provide a method of producing substituted oxystyrene derivatives not associating the disadvantages as described above and insuring easy operations as well as high yield production.

The this inventor earnestly made research activities to develop a method of easily methylenating only an aldehyde group in substituted oxybenzaldehyde without changing a substituted oxy group therein and also without using any specific reagent nor facility, and found that, when substituted oxybenzaldehyde is reacted with dibromomethane in an organic solvent in the presence of an active chloride as well as of zinc metal, the aldehyde group is selectively converted to an ethylene group, and that styrene having a desired substituted oxy group can easily be obtained at a high yield without using any specific facility, and completed this invention based on this discovery.

The present invention relates to a method of producing styrene derivatives expressed the general formula (2) by reacting a benzaldehyde derivative expressed by the general formula (1) with dibromomethane in the presence of zinc metal as well as an active chloride:

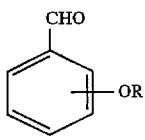 (1)

(wherein R indicates a an alkyl group, alkoxyalkyl group, an alkylcarbonyl group, an alkoxycarbonyl group, a 5 or 6-atom heterocylclic groups, or an alkylsilyl group);

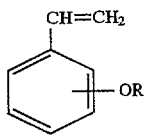 (2)

(wherein R indicates any of the same substituents as those described above.)

DETAILED DESCRIPTION OF THE INVENTION

The substituted oxybenzaldehyde according to the present invention as expressed by the general formula (1) above comprises benzaldehyde and a substituent added to the benzaldehyde such as an alkoxy group, an alkoxyalkyloxy group, an alkylcarbonyloxy group, an alkoxycarbonyloxy group, 5 or 6-atom heterocyclic oxy group including an oxygen atom, or an alkylsilyloxy group. The alkoxy group described above includes a methoxy group, an ethoxy group, a propoxy group, and a tert-butoxy group; the alkoxyalkyloxy group includes a methoxymethoxy group, an ethoxymethoxy group, a 1-ethoxyethoxy group, a 1-isopropoxyethoxy group, a 2-methoxypropoxy group; the alkylcarbonyloxy group includes an acetoxy group, a propionyloxy group, and a butyryloxy group; and the alkoxy alkoxycarbonyloxy group includes a methoxycarbonyloxy group, an ethoxycarbonyloxy group, a tert-buthoxycarbonyloxy group; the 5 or 6-atom heterocyclic group having an oxygen atom includes a tetrahydrofuranyloxy group, and a tetrahydropyranyloxy group. The alkylsilyloxy group includes a tert-butyl dimethylsilyloxy group, and a trimethylsilyloxy group.

The compounds expressed by the general formula (1) above include alkoxy benzaldehydes such as o, m, or p-methoxy benzaldehydes, or o, m, or p-tert-butoxy benzaldehydes; alkoxyalkyloxybenzaldehydes such as o, m, or p-methoxymethoxybenzaldehydes; alkylcarbonyloxy benzaldehydes such as o, m or p-acetoxybenzaldehydes, o, m, or p-propionyloxybenzaldehydes, o, m or p-butyryloxy benzaldehydes; alkoxycarbonyloxy benzaldehydes such as o, m, or p-tert-butoxycarbonyloxybenzaldehydes; 5 or 6-atom heterocyclic substituted benzaldehydes having an oxygen atom such as o,m or p-tetrahydropyranyloxybenzaldehydes, o, m or p-tetrahydrofuranyloxy benzaldehydes; and alkylsilyloxy benzaldehydes such as o, m, or p-tert-butylmethylsilyl benzaldehydes, o, m or p-tert-trimethylsilyloxy benzaldehydes.

The dibromomethane used in the present invention is used as methylenating reagent for methylenating an aldehyde group in the benzaldehyde derivative expressed by the general formula (1) as described above and is generally dibromomethane. A quantity of dibromomethane used according to the present invention is in a range from 1 to 10 mol, and preferably in a range from 1 to 2 mol against 1 mol of the benzaldehyde derivative. It should be noted that, when a quantity of dibromomethane used according to the present invention is less than 1 mol, a yield of the styrene derivative as expressed by the general formula (2), which is a target product for this reaction, becomes disadvantageously lower. Also a quantity of over 10 mol gives no effect to the reaction, but is not economically preferable because the productivity per unit volume of the reactor becomes lower and also because a quantity of dibromomethane not reacting increases.

As the zinc metal used according to the present invention, there are a commercially available product with high purity of zinc metal (99.9%) and the other type of product with low purity thereof (85%), and either type of zinc metal insures a smooth reaction and can be used in the present invention. Also forms of the commercially available zinc metal include powder, sand, granule, and mossy, and any form of zinc metal may be used in the present invention, but powder form of zinc metal having a small granule diameter is preferable for promoting the reaction smoothly at a high speed. A quantity of zinc metal used according to the present invention is generally in a range from 2 to 20 mol, and preferably in a range from 3 to 5 mol against 1 mole of the benzaldehyde derivative expressed by the general formula (1). The quantity of less than 2 moles is not preferable because a yield of the styrene derivative expressed by the general formula (2) becomes lower, and the quantity exceeding 20 mol give no effect to the reaction, but is industrially disadvantageous because a quantity of zinc metal not reacting disadvantageously increases and also because a quantity of solvent used for the reaction increases in association with increase of not-reacted zinc metal.

The active chloride used in the present invention is an reagent used to selectively and smoothly promote the reaction of dibromomethane by activating the zinc metal. The active chlorides include chlorosilane compounds, alkylchlorosilane compounds, acylchloride compounds, thionyl chloride, anhydrous hydrogene chloride, and acylchlorides such as acethyl chloride. Especially the halogenated silane compounds expressed by the general formula (3), and acylchloride compounds are preferred.

 (3)

(Herein, R indicates a methyl group or an ethyl group, m indicates an integer in a range from 0 to 3, and n indicates an integer in a range from 1 to 3, so that 1+m+n=4)

As the example, it is possible to enumerate ethylchlorosilane, ethyltrichlorosilane, dimethyldichlorosilane, methyldichlorosilane methyltrichlorosilane, trichlorosilane, trimethylchlorosilane, methylchlorosilane, or the like.

A quantity of the active chloride used according to the present invention is generally in a range from 0.002 to 1 mole, and preferably in a range from 0.005 to 0.5 mole against 1 mole of zinc metal. If the quantity is less than 0.002 mole, yield of the styrene derivative expressed by the general formula (2), which is a target product of the reaction, becomes lower, and if the quantity exceeds 1 mol, a quantity of chloride not reacting increases, which is economically disadvantageous. The method according to the present invention may be carried out by setting the zinc metal and active chloride as described above in a reactor together with a benzaldehyde derivative expressed by the general formula (1) as a feed stock and dibromomethane as a reacting agent. In this case, the zinc metal is activated by the chloride in the reactor and promote a smooth reaction between the feed stock and dibromomethane. However, as a large quantity of heat is generated in the initial stage of this reaction and some considerations must be taken to control the reaction temperature, it is industrially preferable to activate the zinc metal with an active chloride and then gradually add a solution obtained by dissolving substituted oxybenzaldehyde and dibromemethane as feed stocks into the reaction mixture. In this case, metallic zinc powder is mixed and agitated in the reaction solution, the mixture solution is heated up to the reaction temperature, and then a prespecified quantity of active chloride is dropped for activation. When a nitrogen-containing polar organic solvent such as acetonitrile, or N,N-dimethylfolmaldehyde is used as a solvent to be used for the purpose of the present invention, the reaction goes smoothly, and the styrene derivative as expressed by the general formula (2) can be obtained at a high yield.

Preferable solvents, which can be used for the purpose of the present invention, include N,N-dimethyl folmaldehyde, N,N-dimethylacetoamide, N-methyl-2-pyrrolydone, and 1,3-dimethyl-2-imidazolydinone.

In the reaction according to the present invention, the benzaldehyde derivative feed stock expressed by the general formula (1), dibromomethane, and zinc metal previously activated by an active chloride, or an active chloride are reacted with zinc metal in the solvent described above under a temperature of less than 100° C. or less, and preferably under a temperature of 80° C. or less. The reaction temperature exceeding 100° C. is not preferable because a yield of the styrene derivative expressed by the general formula (2) becomes lower.

After the completion of the reaction, sometimes there may be, in addition to the target compound, such zinc compounds as zinc metal not reacted yet, activated zinc metal, and zinc bromide in the reaction products, which may impede separation and refine of the styrene derivative expressed by the general formula (2), which is the target compound for the reaction. Especially polymerization of substituted oxystyrene, which is the target compound, may be caused by activated zinc metal, zinc chloride which is a Lewis acid compound, or the like. To eliminate effect by the activated zinc metal as described above, a saturated ammonium chloride aqueous solution may be added thereto. Then the activated zinc compound loses its activity due to water, and zinc bromide can form a complex with ammonium chloride and migrate into the aqueous solution, thus being inactivated. In this case, a quantity of saturated ammonium chloride aqueous solution to be added should preferably in a range from 1 to 3 mol in terms of ammonium chloride against 1 mol of zinc metal. The same effect can be achieved by using saturated ammonium bromide aqueous solution.

When acyloxystyrene is synthesized according to the present invention, the target compound is hydrolyzed and vinylphenol is generated, and for this reason it is preferable to add an corresponding acid anhydride after the completion of the methylenating reaction and conduct the acylating reaction again for improving the yield of the target compound.

It should be noted that the procedure to react the substituted oxybenzaldehyde according to the present invention with dibromomethane, metallic zinc, and an activating chloride for obtaining substituted oxystyrene is novel.

DESCRIPTION OF THE PREFERRED EMBODIMENTS

Next detailed description is made for the present invention with referent to embodiments thereof.

[Embodiment 1]

Synthesis of feed stock p-acetoxybenzaldehyde (PABA)

300 g of p-hydroxybenzaldehyde (2.459 mol) and 574 g of water were prepared in a four necked flask having the capacity of 3 l and equipped with an agitator, a cooling tube, a thermometer, and a dropping funnel, and then 410 g of 48% NaOH aqueous solution (4.918 moles) was dropped under the room temperature. 450 g acetic anhydride (3.688 mol) was dropped for 2 hours under the room temperature. After the end of dropping, the post reaction was carried out for 2 hours.

After 600 g of toluene was added to and mixed in the resultant reaction products, the mixture was left for a while for separation. Then the aqueous layer was separated and removed. The toluene layer obtained as described above was washed with 400 g of water.

Toluene was distilled off by means of vacuum distillation from the toluene layer obtained as described above. A weight of the residue in the reactor as described above was 380 g, and the content of p-acetoxybenzaldehyde was 98.8%. The yield based on p-hyroxybenzaldehyde was 94%. The residue obtained as described above was used as a feed stock for the following methylenating reaction.
Synthesis of p-acetoxystyrene
<Activation of zinc metal>

418.7 g (6.40 mol) of zinc powder (produced by Katayama Kagaku with the purity of 85%) and 1400 g of anhydrous N,N-dimethyl folmaldehyde (DMF) were placed in a four necked flask having the volume of 5 l and equipped with an agitator, a condenser, a thermometer, and a dropping funnel, and was agitated to substitute it with nitrogen and heated up to 50° C. then 12.3 g of acethyl chloride (0.157 mol) was dropped for 15 minutes. Then agitation was continued for 15 minutes under the same temperature to completely activate the zinc metal.
<Methylenating reaction>

Then a mixture solution consisting of 280 g of p-acetoxybenzaldehyde (1.7070 mol) and 445 g of dibromomethane (2.561 mol) was dropped for 2 hours keeping the temperature inside the flask at 50° C. Then the post reaction was carried out for 30 minutes under the same temperature. Then under the same temperature, 74 g of acetic anhydride (1.708 mol) was dropped for 15 minutes, and furthermore the post reaction was continued for 30 minutes.

Molar ratios of feed stocks used in the reactions are as shown in Table 1.

TABLE 1

| |
|---|
| Molar ratio of Zn/PABA = 3.75 |
| Molar ratio of acetyl chloride/Zn = 0.02 |
| Molar ratio of $CH_2Br_2$/PABA = 1.5 |
| Molar ratio of acetic anhydride/PABA = 1.0 |
| Weight ratio of DMF/PABA = 5.0 |

A aliquot of the reaction product was sampled and the composition was analyzed by way of liquid chromatography, and the result was as shown in Table 2.

TABLE 2

| | |
|---|---|
| p-hydroxybenzaldehyde | 0.09 mole % |
| p-acetoxybenzaldehyde | 0.13 |
| p-vinyl phenol | 1.86 |
| p-acetoxystyrene | 80.20 |
| Other by-products (polymer) | 17.72 |

From the result of analysis shown in Table 2, the reaction results as shown in Table 3 was obtained.

TABLE 3

| | |
|---|---|
| Conversion of p-acetoxybenzaldehyde | 99.8 mol % |
| Selectivity of p-acetoxystyrene | 80.4 mol % |
| Yield of p-acetoxystyrene | 80.2 mol % |

<Post treatment>

After the end of the reaction, the reaction product was cooled down to 0° C. Then, 1169 g of saturated ammonium chloride aqueous solution (content of $NH_4Cl$: About 29%) was added cooling, and was agitated therein. Then 57 g of radiolite was added as a filtering promoter and the suspended non reacted zinc was filtered off. Then 300 g of toluene was spread over the obtained cake for washing.

The toluene liquid for washing was combined with the filtrate, then 553 g of toluene was added to the combined liquid, and p-acetoxystyrene, which was the target composition, was extracted in the toluene layer. Then 415 g of toluene was added, and same operation for extraction was repeated twice. The total weight of toluene extract obtained as described above was 1630 g.

Then toluene was distilled from the toluene extract keeping the temperature inside the reactor at 60° C. or less under reduced pressure 10 to 140 mmHg. Weight of the residue was 261 g.

Then the residue in the reactor was transferred into a vacuum distillation device, 0.02 g of 2-tert-butyl hydroqinone was added as a polymerization inhibitor, and distillation was carried out under reduced pressure from 1 to 2 mmHg. The initial distillate was cut off and then 176 g of p-acetoxystyrene having a boiling point range from 75° to 76° C./1 mmHg (literature reported value: 73° to 75° C./0.6 mmHg) was obtained.

The obtained p-acetoxystyrene was a transparent liquid having no color, and the purity was 98.5% (GC). No polymer was found in analysis with GPC.

The total yield from the reaction up to separation was 63 mole % (based on p-acetoxybenzaldehyde).

Spectrum data of the p-acetoxystyrene obtained as described above is as shown below.
Infrared spectrum (KBr)
Peak absorbed wave number (ν max) cm-1
1755, 1500, 1365, 1190, 1180
$H^1$-NMR spectrum
δ ppm: 2.30 (s), 5.25 (d), 5.71 (d), 6.71 (dd), 7.05 to 7.44 (m)
MASS spectrum (m/e)
M/Z: 160 ($M^+$), 120 ($M^+$-$COCH_3$), 105 ($M^+$-57), 94 ($M^+$-68), 91 ($M^+$-71)

[Embodiment 2]

Synthesis of p-acetoxystyrene 58.9 g (0.9 mol) of zinc powder (produced by Katayama Kagaku with the purity of 85%) and 164 g of DMF anhydrous were prepared in four necked flask having the volume of 1 l and equipped with an agitator, a condenser, a thermometer, and a dropping funnel and was agitated to substitute it with nitrogen. Then a solution consisting of 3.9 g of trimethyl chlorosilane (0.036 mole) and 19.6 g of anhydrous DMF was dropped for 15 minutes keeping the internal temperature in the reactor at 50° C. Then the reaction mixture was continuously agitated for 15 minutes under the same temperature.

Then a mixture obtained by mixing 32.8 g of p-acetoxybenzaldehyde (PABA) (0.2 mol) and 52.15 g of dibromomethane (0.3 mol) in 85 g of anhydrous DMF was dropping for 1 hour keeping the internal temperature at 50° C. Then agitation was continued for 40 minutes under the same temperature.

Molar ratios in the feed stock are as shown in Table 4.

TABLE 4

| | |
|---|---|
| Molar ratio of Zn/PABA | 4.5 |
| Molar ratio of $(CH_3)_3SiCl/Zn$ | 0.04 |
| Molar ratio of $CH_2Br_2$/PABA | 1.5 |
| Weight ratio of DMF/PABA | 8.2 |

After the completion of reaction, a aliquot of the reaction product was sampled and analyzed by means of liquid chromatography, and the result was as shown in Table 5.

TABLE 5

| | |
|---|---|
| p-hydroxybenzaldehyde | 1.57 mol % |
| p-acetoxybenzaldehyde | 0.86 |
| p-vinyl phenol | 16.79 |
| p-acetoxystyrene | 69.75 |
| Other by-products (polymer) | 11.03 |

From a result of analysis as shown in Table 5, a result of the reaction was as shown in Table 6.

TABLE 6

| | |
|---|---|
| Conversion of p-acetoxybenzaldehyde | 97.6 mol % |
| Selectivity of p-acetoxystyrene | 69.8 mol % |
| Yield of p-acetoxystyrene | 16.8 mol % |

[Embodiment 3]

Synthesis of p-acetoxystyrene
<Activation of zinc metal>

73.6 g of metallic zinc powder (produced by Katayama Kagaku with the purity of 85%) (1.126 mole) and 246 g of anhydrous N, N-dimethyl formaldehyde (DMF) were placed in a four necked flask having the capacity of 1 l and equipped with an agitator, a condenser, a thermometer, and a dropping funnel, and was agitated to substitute it with nitrogen, and heated to 50° C. then 3 g of trimethyl chlorosilane (0.0276 mol) was dropped for 5 minutes. Then the reaction mixture was continuously agitated for 15 minutes under the same temperature to completely activate the zinc metal.
<Methylenating reaction>

Then a mixture solution consisting of 49.2 g of p-acetoxybenzaldehyde (0.3 mol) and 78.2 g of dibromomethane (0.45 mol) was dropped for 90 minutes keeping the internal temperature at 50° C. Then the reaction was continued for 30 minutes under the same temperature.

Then 32 g of acetic anhydride (0.3 mol) was dropped for 55 minutes keeping the same temperature.

Molar ratios of feed stocks were as shown in Table 7.

TABLE 7

| | |
|---|---|
| Molar ratio of Zn/PABA | 3.75 |
| Molar ratio of trimethyl chlorosilane/Zn | 0.02 |
| Molar ratio of $CH_2Br_2$/PABA | 1.5 |
| Molar ratio of acetic anhydride/PABA | 1.0 |
| Weight ratio of DMF/PABA | 5.0 |

A aliquot of the reaction product was sampled and the composition was analyzed by means of liquid chromatogrpahy, and the result was as shown in Table 8.

TABLE 8

| | |
|---|---|
| p-hydroxybenzaldehyde | 0 mol % |
| p-acetoxybenzaldehyde | 0.55 |
| p-vinyl phenol | 2.22 |
| p-acetoxystyrene | 81.10 |
| Other by-products (Polymer) | 16.13 |
| Conversion of p-acetoxybenzaldehyde | 99.9 mol % |
| Yield of p-acetoxystyrene | 81.1 mol % |

<Post treatment>

After the completion of the reaction, the reaction products were cooled down to 0° C. Then 208 g of saturated ammonium chloride aqueous solution (content of $NH_4Cl$: About 29%) was added, being cooled, to the reaction product, and the mixture was agitated and mixed. Then 10 g of radiolite was added as a filtering support, and the suspended zinc not reacted yet was filtered. Then 60 g of DMF was spread over the obtained cake for washing.

Then the DMF liquid and the filtrate were combined, 253 g of toluene was added to the combined liquid, and p-acetoxystyrene, which was the target material, was extracted in the toluene layer. The similar operation for extraction was repeated twice.

Then toluene was distillated and removed from the toluene extract keeping the temperature in the reactor at 60° C. or less in the state where the pressure was lowered to a range from 10 to 140 mmHg. Weight of the residue on distillation obtained as described above was 53.1 g.

Then the residue material in the reactor was transferred into a vacuum distillation device, 0.005 g of 2-tert-butylhydroqinone was added as a polymerization inhibitor and distillation was conducted in the depressurized state from 1 to 2 mmHg. The initial distilled material was cut, and 28 g of p-acetoxystyrene having the boiling point of 82° to 83° C./2 mmHg was obtained.

The obtained p-acetoxystyrene was a transparent liquid having no color, and the purity was 98.6% (GC). No polymer was detected in analysis with GPC.

The total yield from the reaction to separation was 57 mole % (based on p-acetoxybenzaldehyde).

[Embodiment 4]

Synthesis of o-acetoxybenzaldehyde which is a feed stock 150 g of salycylic aldehyde (1.23 mol) triethyl amine (1.48 mol) and 300 g of toluene were prepared in a four necked flask having the capacity of 1 l and equipped with an agitator, a condenser, a thermometer, and a dropping funnel, and 151 g of acetic anhydride (1.48 mol) was dropped for 1 hour keeping the reaction temperature in a range from 21° to 26° C. After the completion of dropping, the temperature was raised to 50° C. and the post reaction was conducted for 2 hours.

150 g of water was added to the obtained reaction product and the mixture solution was agitated, and then was quietly left for separation. Then the water layer was separated and removed. The same operation for washing was repeated once more.

The toluene layer washed as described above was subjected to vacuum distillation for removing toluene. 207 g of the obtained residue in the reactor was transferred into a vacuum distillation device, distillation was conducted under a reduced pressure of 3 mmHg, and 137 g of distillate having the boiling point in a range from 86° to 92° C./3 mmHg was obtained. Content of o-acetoxybenzaldehyde in this distilled material was 99.6%.

Yield based on o-hydroxybenzaldehyde was 68 mole %.

Synthesis of o-acetoxystylene
<Activation of zinc metal>

193.7 g of zinc powder (produced by Katayama Kagaku with the purity of 85%) (2.96 mol) and 650 g of anhydrous N, N-dimethylfolmaldehyde (DMF) were prepared in four necked flask having the volume of 2 l and equipped with an agitator, a condenser, a thermometer, and a dropping funnel, and were agitated to substitute it with nitrogen and heated to 50° C. then 6.2 g of acetyl chloride (0.1 mol) was dropped for 10 minutes. Then agitation was continued for 20 minutes under the same temperature to completely activate the zinc metal.

<Methylenating reaction>

Then a mixture solution consisting of 114 g (0.79 mol) of o-acetoxybenzaldehyde described above and 207 g of dibromomethane (1.19 mol) was dropped for 3 hours keeping the internal temperature at 50° C. Then the post reaction was continued for 30 minutes under the same temperature.

Then keeping the same temperature, 80.6 g of acetic anhydride (0.79 mol) was dropped for 30 minutes, and furthermore the post reaction was continued for 30 minutes.

A aliquot of the reaction products was sampled and the composition was analyzed by means of liquid chromatography. As a result, the conversion of o-acetoxybenzaldehyde was 99.4%, while the yield of o-acetoxystylene was 48 mole %.

<Post treatment>

After the end of the reaction, the reaction product was cooled down to 0° C. Then 587 g of aqueous saturated ammonium chloride solution (concentration of $NH_4Cl$: About 29 %) was added, being cooled, to the reaction product, and was fully agitated. Then 26 g of radiolite was added as a filtering promoter, and the suspended zinc not reacted yet was filtered.

Then 256 g of toluene was added to the filtrate for extraction, and o-acetoxystylene, which was a target material, was extracted in the toluene layer. The similar operation for extraction was repeated 3 times, adding 192 g of toluene each time, and the yield through the reaction was 48 mole % (based on o-acetoxystylene).

Then keeping the internal temperature at 60° C. and less under the reduced pressure in a range from 10 to 140 mmHg, and toluene was distilled from the toluene extraction liquid. Weight of the obtained residue in the reactor was 130 g.

Then the residue was transferred to a vacuum distillation device, 0.02 g of 2-tert-butyl hydroqinone was add as a polymerization inhibitor, and distillation was conducted under the reduced pressure in a range from 1 to 2 mmHg. The initial distillate was cut, and then 70 g of o-acetoxystylene having the boiling point in a range from 72° to 85° C./4 mmHg was obtained.

The obtained o-acetoxystylene was a transparent solution having no color, and the purity was 91.7% (GC). No polymer was detected in the GPC analysis.

The total yield from the reaction to the separation was 33 mole % (based on o-acetoxybenzaldehyde).

[Embodiment 5]

Synthesis of m-acetoxybenzaldehyde which is a feed stock 100 g of m-hydroxybenzaldehyde (0.82 mol), 138.4 g of triethylamine (0.984 mole), and 200 g of toluene were prepared in a four necked flask having the volume of 1 l and equipped with an agitator, a condenser, a thermometer, and a dropping funnel, and 100 g of acetic anhydride (0.98 mol) was dropped, being cooled for 2 hours. After the completion of dropping, the post reaction was continued for 1 hour.

100 g of water was added to the reaction products obtained as described above, and was quietly left for separation. Then the water layer was separated and removed. The same operation for washing was repeated twice and then the reaction products were washed with water. The toluene layer washed as described above was subjected to vacuum distillation to remove toluene. The obtained residue in the reactor was transferred to a vacuum distillation device, distillation was conducted under the reduced pressure of 5 mmHg, and 114 g of distillate having the boiling point in a range from 124° to 127° C./5 mmHg was obtained. Content of m-acetoxybenzaldehyde in the distillate was 98.8%.

The yield based on m-hydroxybenzaldehyde was 85%.
Synthesis of m-acetoxystyrene
<Activation of zinc metal>

170.5 g (2.61 mol) of zinc powder (produced by Katayama Kagaku with the purity of 85%) and 570 g of anhydrous N, N-dimethylfolmaldehyde (DMF) were placed in a four necked flask having the volume of 2 l and equipped with an agitator, a condenser, a thermometer, and a dropping funnel, and were agitated to substitute it with nitrogen, and heated to 50° C. then 5.5 g of acetyl chloride (0.157 mol) was dropped for 15 minutes. Then agitation was continued for 15 minutes under the same temperature to completely activate the metallic zinc.
<Methylenating reaction>

Then a mixture solution consisting of 114 g of m-acetobenzaldehyde (0.695 mol) and 181 g of dibromomethane (1.04 mol) was dropped for 2 hours keeping the internal temperature at 50° C. Then the post reaction was continued for 30 minutes under the same temperature.

Then 70.9 g of acetic anhydride (0.695 mol) was dropped for 15 minutes keeping the same temperature, and furthermore the post reaction was continued for 30 minutes.

A aliquot of the reaction product was sampled and the composition was analyzed by means of liquid chromatography. As a result, the conversion of m-acetoxybenzaldehyde was 99.7%, and the yield of m-acetoxystyrene was 77%.
<Post treatment>

After the completion of the reaction, the reaction products were cooled down to 0° C. Then, 439 g of saturated ammonium chloride aqueous solution (concentration of NH$_4$Cl: About 29%) was added, being cooled, to the reaction products, and was fully agitated. Then 23 g of radiolite was added as a filtering support, and the suspended zinc unreacted was filtered. Then 200 g was added to the filtrate and m-acetoxystyrene, which was a target material, was extracted in the toluene layer. The same operation for extraction was repeated twice, adding 150 g and 100 g of toluene respectively. The total weight of toluene extract obtained as described above was 609 g.

Then keeping the internal temperature at 60° C. under the reduced pressure in a range from 10 to 140 mmHg, toluene was removed from the toluene extract. Weight of the obtained residue was 117 g.

Then the residue was transferred to a vacuum distillation device, 0.02 g of 2-tert-butyl hydroqinone was added, and distillation was conducted under the reduced pressure in a range from 1 to 2 mmHg. The initial distillate was cut off and 64 g of m-acetoxystyrene having the boiling point from 98° to 102° C./2.5 mmHg was distillated.

The obtained m-acetoxystyrene was a transparent liquid having no color, and the purity was 98.7% (GC). No polymer was detected in the GPC analysis.

The whole yield from the reaction to separation was 57 mole % (based on m-acetoxybenzaldehyde).

[Embodiment 6]

Synthesis of p-tert-butoxycarbonyloxy benzaldehyde which is a feed stock 100 g of p-hydroxybenzaldehyde (0.8 mol), 300 g of dioxane, and 197 g of di-t-butyldicarbonate (0.9 mol) were placed in a four necked flask having the volume of 1 l and equipped with a dropping funnel, a condenser, a thermometer, and an agitator, and 91.1 g (0.9 mol) of triethylamine was dropped for 1 hour keeping the reaction temperature at 30° C. Then, the post reaction was continued for 2 hours under the same temperature. The conversion of p-hydroxybenzaldehyde was 98%. After the completion of the reaction, 600 g of the reaction products and 1500 g of ethylether were added to the reaction products and the mixture was agitated, and then was quietly left for separation. Then the oil layer was washed with water and was dried with MgSO$_4$. Then ethylether was distilled off and dried, and 366 g of n-hexane was added to the residual liquid, and the mixture liquid was cooled down to 20° C. to conduct an operation for crystallization. After the precipitated crystal was filtered, the wet crystal was dried for 4 hours under a temperature of 30° C. under a reduced pressure of 20 mmHg, and 149 g of crystal of p-butoxycarbonyloxy benzaldehyde (0.6 mol) was obtained. The purity of p-tert-butoxycarbonyloxy benzaldehyde was 99.5%, and the yield was 82% (based on p-hydroxy benzaldehyde).
Synthesis of p-tert-butoxycarbonyloxystyrene
<Activation of zinc metal>

49 g of zinc powder (produced by Katayama Kagaku with the purity of 85%) (0.75 mol) was placed in a four necked flask having the volume of 1 l and equipped with an agitator, a condenser, a thermometer and a dropping funnel, and was agitated by substituting the systems with nitrogen and heated to 50° C. Then acetyl chloride 1.4 g (0.018 mol) was gradually dropped for 30 minutes keeping the internal temperature at 50° C. Agitation was continued for 15 minutes to completely activate the zinc metal.
<Methylenating reaction>

Then 44 g of p-tert-butoxycarbonyloxy benzaldehyde synthesized as described above (0.2 mol) and 52 g (0.2 mol) of dibormomethane (0.3 mol) were dropped to the metallic zinc suspension as described above for 1 hour keeping the reaction temperature in a range from 50° to 53° C. The reaction proceeded generating heat. Then the post reaction was continued for 30 minutes keeping the same temperature.
<Post treatment>

After the completion of the reaction, the reaction products were cooled down to the room temperature. Then, 138 g of aqueous saturated ammonium chloride solution (concentration of NH$_4$Cl: About 29%) was added to the reaction products, and the mixture was fully agitated. Then 6.7 g of radiolite commercially available was added as a filtering support and zinc metal unreacted was filtered.

220 g of toluene was added to the filtrate obtained as described above, and p-tert-butoxycarbonylstyrene, which was the target material, was extracted in the toluene layer. The operation for extraction was repeated twice. The extraction was analyzed by means of liquid chromatography and the reaction yield was calculated, and it was found that the yield was 93%.

Then the extraction liquid described above was subjected to vacuum distillation keeping the internal temperature at 100° C. or less to distillate toluene. Then the residue in the reactor was transferred into a vacuum distillation device, and distillation was conducted under the reduced pressure in a range from 1 to 2 mmHg. The initial distillate was cut off and 38.3 g of p-tert-butoxycarbonyloxystyrene having the boiling point from 115° to 120° C./1 to 2 mmHg (literature reported value: 90° to 92° C./0.2 mmHg) was distilled.

The obtained p-tert-butoxycarbonyloxystyrene was a transparent liquid having no color, and the purity was 97% (GC). The total yield of the p-tert butoxycarbonyloxystyrene was 87 mole % (based on p-tert-butoxycarbonyloxybenzaldehyde).

Structure of the p-tert-butoxycarbonyloxystyrene obtained as described above was analyzed.

MASS spectrum (m/e)
M/Z: 200 (M$^+$), 205 (M-CH$_3$), 161 (M-59), 147 (M-OBu), 133 (M-87), 120 (M-CO$_3$Bu)

H$^1$-NMR (CDCl3) spectrum
δ mm: 1.55 (S), 5.29 (d), 5.73 (d), 6.69 (dd), 7.25–7.42 (m)

IR spectrum (ν max) cm$^{-1}$
2980, 1755, 1501, 1375, 1280, 1260, 1220, 1150

| | Elemental analysis | |
|---|---|---|
| | Calculated value | Found value |
| C | 70.89% | 69.86% |
| H | 7.32% | 7.16% |

[Embodiment 7]

Synthesis of p-tetrahydropyrano(2)oxybenzaldehyde which is a feed stock 28.5 g of p-hydroxybenzaldehyde (0.234 mol), 59 g of 3,4-dihydro-2H-pyrane (0.701 mol), and 57 g of ethylacetate were placed in a four necked flask having the volume of 500 ml and equipped with an agitator, a cooling tube, a thermometer, and a dropping funnel, and 12.7 ml of ethylacetate solution with saturated hydrogen chloride was dropped cooling the flask with ice. Then the reaction was continued for 47 hours being agitated under the room temperature.

After the completion of the reaction, the reaction products were dissolved in 187 g of NaOH aqueous solution, and the target material was extracted with 500 g of ethylacetate. After the water layer was removed, furthermore using 187 g of 5% NaOH aqueous solution, p-hydroxybenzaldehyde unreacted was extracted. Then the obtained oil layer was washed with water, dried with magnesium sulfate, a small quantity of hydrotalcite was added as an acid capture agent, and a minute quantity of hydrogen chloride was removed. Then vacuum distillation was conducted to remove ethylacetate and excess of 3,4-dihydro-2H-pyrane.

In the residue in the reactor was contained p-tertahydropirane (2) oxybenzaldehyde, which was the target material, by 67 weight %, and the weight was 67.7 g. The yield of p-tetrahydropirano(2)oxybenzaldehyde was 97%.

Synthesis of p-tetrahydropyrano(2)oxystyrene

In Embodiment 6, the synthesis was conducted according to the same method as that in Embodiment 6 except that 61.5 g of p-tetrahydropyrano(2)oxybenzaldehyde was used in place of p-tert-butoxycarbonylbenzaldehyde which was a feed stock.

As a result, p-tetrahydropirano(2)oxybenzaldehyde was formed at the yield of 89%. Weight of p-tetrahydropirano (2)oxystyrene distilled and separated by means of vacuum distillation and having the boiling point in a range from 104° to 106° C./2 mmHg (literature reported value: 82° C./0.2 mmHg) was 23.7 g, and the purity was 96% (HPLC). Also the whole yield from the reaction to separation was 58% based on p-tetrahydropirano(2)oxybenzaldehyde.

Spectrum of the p-tetrahydropirano(2)oxystyrene obtained as described above was as shown below.

Infrared spectrum (KBr)
Peak absorbed wave number (ν max) cm$^{-1}$
2940, 1605, 1510, 1240, 1200, 1175, 1120, 1110, 1035, 1020

H$^1$-NMR (CDCl3) spectrum
δ ppm: 1.50–2.10 (m), 3.55–4.10 (m), 5.14 (d), 6.69–7.45 (m)

[Embodiment 8]

50 g of p-hydroxybenzaldehyde (0.4 mol) and 500 g of DMF were placed in a four necked flask having the volume of 1 l and equipped with an agitator, a condenser, a thermometer, and a dropping funnel, and the system was substituted with nitrogen. Then 69.8 g (1.03 mol) of imidazole was dropped. Then 92.7 g of t-butyl dimethylchlorosilane (0.615 mol) was dropped cooling the flask with ice. The reaction was continued for 15 hours cooling the flask with ice.

After the completion of the reaction, the reaction products were poured into 500 g of water, and the target material was extracted with 500 g of ethylacetate. Furthermore this operation for extraction was repeated twice. The obtained extract was washed with 5% NaOH aqueous solution, and then washed with water. Then ethylacetate was recovered by means of vacuum distillation, and furthermore the bottom temperature and a degree of vacuum were raised (100° C., 3 mmHg) to remove evaporative components. Weight of the obtained residue in the reactor was 88.5 g, and the content of p-t-butyldimethylsilyl oxybenzaldehyde, which was the target material, was 91.4% (0.34 mol) with the yield of 85% (based on p-hydroxybenzaldehyde).

Synthesis of p-t-butyl dimethyloxystyrene

In the method according to Embodiment 6, synthesis of p-t-butyldimethylsilyloxystyrene was conducted except that 51.6 g (0.2 mol) of the p-t-butyldimethylsilyloxybenzaldehyde described above was used in place of the p-tertbutoxycarbonyloxybenzaldehyde, which was a feed stock.

As a result, p-t-butyldimethylsilyloxystyrene, which was the target material, was obtained at the yield of 84 mole %. Weight of p-t-butyldimethyloxystyrene separated by means of distillation and having the boiling point in a range from 90° to 92° C./3 mmHg (literature value: 80° C./0.1 mmHg) was 25.7 g, and the purity was 97% (HPLC). The whole yield from the reaction to isolation was 55 mol % (based on p-butyldimethylsilyloxybenzaldehyde).

Spectrum of the p-t-butyldimethylsilyloxystyrene obtained as described above was as shown below.

Infrared spectrum (KBr)
Peak absorbed wave number (ν max) cm$^{-1}$
1000, 1505, 1260

H$^1$-NMR
δ ppm: 0.40 (s), 1.00 (s), 5.20 (d), 5.60 (d), 6.55–7.45 (m)

[Embodiment 9]

Synthesis of p-tetrahydrofuryl (2) oxybenzaldehyde 62.2 g (0.510 mol) of p-hydroxybenzaldehyde, 107.2 g (1.530 mol) of 2,3-dihydrofurane, and 124 g of ethyl acetate were placed in a four necked flask having volume of 1 l and equipped with an agitator, a condenser, a thermometer, and a dropping funnel, and 27.7 ml of ethyl acetate with saturated hydrogen chloride therein was dropped cooling the flask. Then the reaction was continued for 5 hours, the solution being agitated, under the room temperature.

After the completion of the reaction, the reaction products were poured into 408 g of 5% NaOH aqueous solution, and the target material was extracted with 500 g of ethyl acetate. After the water layer was separated and removed, furthermore p-hydroxy benzaldehyde unreacted was extracted and removed using 408 g of 5% NaOH aqueous solution. Then, after the obtained oil layer was washed with water, the oil layer was dried with magnesium sulfate, and furthermore a small quantity of hydrotalcite was added as an acid capture agent to remove a minute quantity of hydrogen chloride. Then ethylacetate and excess of 2,3-dihydrofurane was distilled off for separation by means of vacuum distillation.

Content of p-tetrahydrofuryl (2) oxybenzaldehyde was 59 weight %, and the weight was 68.1 g. The yield of p-tetrahydrofuryl (2) oxybenzaldehyde was 41 mole %.

Synthesis of p-tetrahydrofuryl (2) oxystyrene

Synthesis of p-teetrahydrofuryl (2) oxystyrene was conducted according to the same method as that employed in Embodiment 6 except that 65.1 g (0.2 mol) of p-tetrahydrofuryl (2) oxybenzaldehyde was used as a feed stock in place of p-tert-butoxycarbonyloxybenzaldehyde, which was a feed stock.

As a result, the yield through the reaction was 42 mol % and the weight of distilled p-tetrahydrofuryl (2) oxystyrene, which was the target material, was 11.4 g with the purity of 92% (HPLC). Also the whole yield from the reaction to isolation was 30 mol % based on p-tetrahydrofuryl (2) oxybenzaldehyde.

Spectrum of p-tetrahydrofuryl (2) oxystyrene obtained as described above was as shown below.

Infrared spectrum (KBr)
Peak absorbed wave number (ν max) cm$^{-1}$
1605, 1505, 1240, 1075, 1040

H$^1$-NMR spectrum (CDCl3)
δ ppm; 1.80–2.90 (m), 3.60–4.60 (m), 5.22 (d), 5.55–5.90 (m), 6.69 (dd), 7.00–7.53 (m)

[Embodiment 10]

Synthesis of p-methoxymethoxybenzaldehyde 69.5 g (0.57 mol) of p-hydroxybenzaldehyde, 500 g of toluene, and 30 g of methanol were placed in a four necked flask having the volume of 1 l and equipped with an agitator, a condenser, a thermometer, and a dropping funnel, and the system were substituted with nitrogen, and the mixture solution was heated up to 70° C. Then 131 g (0.68 mol) of 28% CH$_3$ONa solution was dropped for 25 minutes, and furthermore the reaction was continued for 2 hours under the same temperature. Then, after methanol was distilled off, the reaction products were cooled down to 5° C. Then 54.7 g (0.68 mol) of monochloromethyl ether (ClCH$_2$OCH$_3$) was dropped for 30 minutes keeping the temperature at 5° C., and furthermore the reaction was continued for 20 hours.

328 g of 5% NaOH aqueous solution and 500 g of toluene were added to the obtained reaction products, and p-hydroxy benzaldehyde was extracted in the aqueous layer. Then, the oil layer was washed with water, dried with magnesium sulfate, and toluene and monochloromethyl ether unreacted were distilled off. Weight of obtained residue in the reactor was 35 g, and the residue was p-methoxybenzaldehyde with the purity of 99.1%. The yield of p-hydroxy benzaldehyde was 37 mole %.

Synthesis of p-methoxymethoxystyrene

Synthesis of p-methoxystyrene was conducted according to the same method as employed in Embodiment 6 except that 33.2 g of p-methoxymethoxybenzaldehyde (0.2 mol) was used in place of the tert-butoxycarbonylbenzaldehyde, which was a feed stock, was used.

As a result, 10.0 g of p-methoxystyrene having the boiling point in a range from 92° to 93° C./4 mmHg (literature reported value: 93°–94° C./4 mmHg) was distilled and separated, and the purity was 94.8%.

The whole yield from the reaction to isolation was 58 mole % based on p-methoxymethoxybenzaldehyde.

Spectrum of the obtained p-methoxystyrene was as shown below.

Infrared spectrum (KBr)
Peak absorbed wave number (ν max) cm$^{-1}$
1601, 1501, 1236, 1153, 1080, 1005

H$^1$-NMR spectrum
δ ppm: 3.50 (s), 5.20 (d), 5.22 (s), 5.08 (d), 6.70 (dd), 7.00–7.52 (m)

[Embodiment 11]

Synthesis of p-methoxystyrene which is a feed stock

Synthesis of p-methoxystyrene was conducted according to the same method as that employed in Embodiment 6 except that 27.2 g (0.2 mol) of p-anisaldehyde described above was used as a feed stock in place of the tertbutoxycarbonyloxy benzaldehyde.

As a result, yield of the target material was 87%.

Weight of the p-methoxystyrene separated by means of distillation was 19.9 g, and the purity was 98.3%. The whole yield from the reaction to separation was 74 mole % (based on p-anisaldehyde).

Spectrum of the p-methoxystyrene obtained as described above was as described below.

Infrared spectrum (KBr)
Peak absorbed wave number (ν max) cm$^{-1}$
1605, 1510, 1245, 1175

H$^1$-NMR spectrum (CDC 13)
δ ppm: 3.80 (s), 5.08 (d), 5.60 (d), 6.52 (dd), 6.85–7.50 (m)

[Embodiment 12]

The reaction was conducted according to the procedure in Embodiment 2 except that zinc powder with the purity of 99.9% (produced by Koujundo Kagaku K.K.) was used in place of Zn powder with the purity of 85%.

As a result, the conversion of p-acetoxystyrene was 99.8%, and the yield through the reaction was 68% (based on p-acetoxy benzaldehyde).

[Embodiment 13–18]

The reactions were conducted according to the procedure in Embodiment 2 except that N,N-diethylacetamide, N,N-dimethylacetamide, N-methyl-2-pyrrolidone, 1,3-dimethyl-2-imidazolidinone, and acetonitrile solvents were used in place of the reaction solvent of DMF respectively.

A result for each reaction is shown in Table 9.

TABLE 9

Result of Reaction

| Solvent | Conversion (%) | Yield (Mole %) |
| --- | --- | --- |
| N,N-dimethyl acetamide | 97 | 69 |
| N,N-dimethyl acetamide | 98 | 70 |
| N-methyl-2-pyrrolidone | 96 | 68 |
| 1,3-dimethyl-2-imidazolidnione | 98 | 73 |
| Acetonitrile | 97 | 60 |

Conversion, yield: Based on p-acetoxy benzaldehyde

[Embodiment 19–20]

The reaction was conducted according to the same method as employed in Embodiment 2 except that anhydrous hydrogen chloride and thionyl chloride were as active chlorides in place of trimethyl chlorosilane.

A result of the reaction was as shown in Table 10.

TABLE 10

| | Result of Reaction | |
|---|---|---|
| Chloride | Conversion (%) | Yield (Mol %) |
| Anhydrous hydrogen chloride | 95 | 67 |
| Thionyl chloride | 93 | 66 |

Conversion, yield: Based on p-acetoxy benzaldehyde

[Embodiment 21–23]

Each reaction was conducted according to the method in Embodiment 2 except that the reaction temperature was changed to 7° C., 31° C., and 80° C. respectively.

Results of the reactions are as shown in Table 11.

TABLE 11

| | Results of Reactions | |
|---|---|---|
| Reaction temperature (°C.) | Conversion (%) | Yield (Mol %) |
| 7 | 75 | 67 |
| 31 | 98 | 74 |
| 80 | 98 | 53 |

Conversion, yield: Based on p-acetoxy benzaldehyde

[Embodiment 24–27]

Each reaction was conducted according to the method in Embodiment 2 except that a quantity of zinc metal against a quantity of p-acetoxy benzaldehyde was changed to 2.4, 3.0, 3.3, and 3.75 mole times.

Results of the reactions are as shown in Table 12.

TABLE 12

| | Results of Reactions | |
|---|---|---|
| Zn/p-acetoxy benzaldehyde molar ratio | Conversion (%) | Yield (Mol %) |
| 2, 4 | 74 | 57 |
| 3, 0 | 86 | 65 |
| 3, 3 | 95 | 68 |
| 3, 75 | 98 | 70 |

Conversion, yield: Based on p-acetoxy benzaldehyde

[Embodiments 28–29]

The reaction experiments were conducted according to the method in Embodiment 2 except that a quantity of DMF solvent was changed to 3 weight portions, and 5 weight portions against 1 weight portion of p-acetoxy benzaldehyde.

The results of reactions were as shown in Table 13.

TABLE 13

| | Results of Reactions | |
|---|---|---|
| DMF/p-acetoxy benzaldehyde weight ratio | Conversion (%) | Yield (Mol %) |
| 3, 0 | 99 | 69 |
| 5, 0 | 98 | 70 |

Conversion, yield: Based on p-acetoxy benzaldehyde

[Embodiments 30–31]

Each reaction was conducted according to the method in Embodiment 2 except that a quantity of dibromomethane used in the reaction was changed to 1.0, and 1.25 mol times against a quantity of p-acetoxy benzaldehyde.

Results of the reactions were as shown in Table 14.

TABLE 14

| | Results of Reactions | |
|---|---|---|
| Dibromomethane/p-acetoxy benzaldehyde molar ratio | Conversion (%) | Yield (Mol %) |
| 1, 0 | 45 | 45 |
| 1, 25 | 81 | 62 |

Conversion, yield: Based on p-acetoxy benzaldehyde

[Embodiments 32–33]

Each reaction was conducted according to the method in Embodiment 2 except that a quantity of trimethyl chlorosilane added to zinc metal was changed to 0.02, 0.002 mole times.

Results of the reactions were as shown in Table 15.

TABLE 15

| | Results of Reactions | |
|---|---|---|
| Trimethyl chlorosilane/Zn molar ratio | Conversion (%) | Yield (Mol %) |
| 0.02 | 93 | 65 |
| 0.002 | 68 | 50 |

Conversion, yield: Based on p-acetoxy benzaldehyde

[Embodiment 34]

The reaction was conducted according to the method in Embodiment 2 except that the reaction temperature was changed to 110° C.

As a result, a conversion and yield of p-acetoxy benzaldehyde were 98% and 28 mole % respectively.

The reaction was conducted according to the method except that trimethyl chlorosilane was not added.

As a result, a conversion and a yield of p-acetoxy benzaldehyde were 26% and 19 mole % respectively.

As described above, the present invention provides a method which is industrially quite useful and enables production of various types of substitutedoxystyrene, which are monomers for polymerization of photoresist material used in a high density integrated circuit process from raw materials which are easily available and can easily be handled.

What is claimed is:

1. A method of producing styrene derivatives expressed by the general formula (2) comprising the step of:

adding dibromomethane to a mixture comprising a benzaldehyde derivative expressed by the general formula (1), zinc metal, and active chloride in an organic solvent,

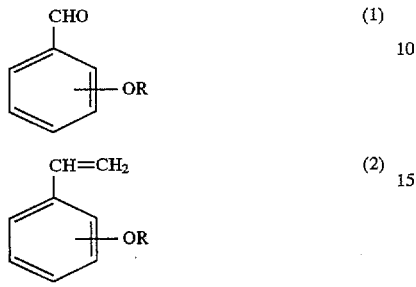

wherein the R group of general formulas (1) and (2) is an alkyl group, an alkoxyalkyl group, an alkylcarbonyl group, an alkoxycarbonyl group, a 5 or 6- atom heterocyclic group, or an alkylsilyl group.

2. The method of claim 1 wherein said R group is a methyl group, a tert-butyl group, an acetyl group, a tert-butoxy carbonyl group, a tetrahydropyranyl group, a tetrahydrofuranyl group, a trimethylsilyl group, a tert-butyl dimethylsilyl group, or a methoxymethyl group.

3. The method of claim 1 wherein the active chloride is an alkylchlorosilane compound, an acyl chloride compound, an anhydrous hydrogen chloride, or thionyl chloride.

4. The method of claim 1, wherein said organic solvent is a nitrogen-containing polar compound.

5. The method of claim 1 wherein said method is carried out at a temperature of less than 100 degrees centigrade.

6. The method of claim 1 wherein said method is carried out at a temperature of less than 80 degrees centigrade.

7. The method of claim 1 wherein said method is carried out at a temperature of approximately 50 degrees centigrade.

8. A method of producing styrene derivatives expressed by the general formula (2) comprising the steps of:

reacting zinc metal with an active chloride thereby generating active zinc metal; and adding a mixture comprising a substituted benzaldehyde expressed by the general formula (1) and dibromomethane in organic solvent to said active zinc metal and active chloride solution;

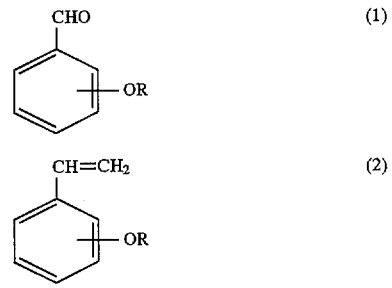

wherein the R group of general formulas (1) and (2) is an alkyl group, an alkoxyalkyl group, an alkylcarbonyl group, an alkoxycarbonyl group, a 5 or 6- atom heterocyclic group, or an alkylsilyl group.

9. The method of claim 8 wherein said R group is a methyl group, a tert-butyl group, an acetyl group, a tert-butoxy carbonyl group, a tetrahydropyranyl group, a terathydrofuranyl group, a trimethylsilyl group, a tert-butyl dimethylsilyl group, or a methoxymethyl group.

10. The method of claim 8 wherein the active chloride is an alkylchlorosilane compound, an acyl chloride compound, an anhydrous hydrogen chloride, or thionyl chloride.

11. The method of claim 8, wherein said organic solvent is a nitrogen-containing polar compound.

12. The method of claim 8 wherein said method is carried out at a temperature of less than 100 degrees centigrade.

13. The method of claim 8 wherein said method is carried out at a temperature of less than 80 degrees centigrade.

14. The method of claim 8 wherein said method is carried out at a temperature of approximately 50 degrees centigrade.

* * * * *